US007642252B2

(12) United States Patent
Brown

(10) Patent No.: US 7,642,252 B2
(45) Date of Patent: Jan. 5, 2010

(54) ANGIOGENESIS INHIBITION BY CEPHALOTAXINE ALKALOIDS, DERIVATIVES, COMPOSITIONS AND USES THEREOF

(75) Inventor: Dennis M. Brown, Menlo Park, CA (US)

(73) Assignee: Chemgenex Pharmaceuticals, Inc., Menlo Park, CA (US)

(*) Notice: Subject to any disclaimer, the term of this patent is extended or adjusted under 35 U.S.C. 154(b) by 0 days.

(21) Appl. No.: 10/625,866

(22) Filed: Jul. 22, 2003

(65) Prior Publication Data

US 2004/0077629 A1    Apr. 22, 2004

Related U.S. Application Data

(60) Provisional application No. 60/397,657, filed on Jul. 22, 2002.

(51) Int. Cl.
    *A61K 31/55*    (2006.01)
(52) U.S. Cl. .................................................. 514/217.05
(58) Field of Classification Search ............. 514/217.08
    See application file for complete search history.

(56) References Cited

U.S. PATENT DOCUMENTS

| 3,793,454 | A | * | 2/1974 | Powell et al. ........... 514/214.01 |
| 4,152,214 | A | | 5/1979 | Delfel et al. |
| 5,380,747 | A | * | 1/1995 | Medford et al. ............. 514/423 |
| 5,712,291 | A | * | 1/1998 | D'Amato ..................... 514/323 |
| 6,025,353 | A | * | 2/2000 | Masferrer et al. ....... 514/210.02 |
| 6,458,829 | B1 | * | 10/2002 | Shen et al. ................... 514/460 |
| 6,630,173 | B2 | | 10/2003 | Brown |
| 6,734,178 | B2 | | 5/2004 | Brown |
| 2001/0049349 | A1 | * | 12/2001 | Chinery et al. ................. 514/1 |
| 2002/0032190 | A1 | | 3/2002 | Brown |

FOREIGN PATENT DOCUMENTS

| JP | 58035146 A | 3/1983 |
| WO | WO 95/29242 | 11/1995 |
| WO | WO 01/68098 | 9/2001 |
| WO | WO02/03904 A | 4/2002 |
| WO | WO 02/32904 | 4/2002 |

OTHER PUBLICATIONS

Cecil Textbook of Medicine, 21st Edition, vol. 1, published 2000, pp. 1060-1074.*
Cecil Textbook of Medicine, 21st Edition, vol. 2, published 2000, pp. 1492-1560, 1551-1554.*
Hawk et al., Primary Cancer Prevention Trials, Hematology/Oncology Clinics of North America, vol. 14, No. 4, Aug. 2000, pp. 809-830.*
Kawai, et al., Cancer Letters, 171 (2001), pp. 201-207.*
O'Dwyer, et al., Journal of Clinical Oncology, vol. 4, No. 10 (Oct. 1986): pp. 1563-1568.*
Medline Abstract No. 97217050, Kumar, Indian Journal of Experimental Biology, (May 1996) 34(5), 391-402.*
Medline Abstract No. 96432582, Oka et al., Japanese Journal of Pharmacology, (Jun. 1996) 71(2), 89-100.*
Medline Abstract No. 97074593, Smith et al., CA: A Cancer Journal for Clinicians, (Nov.-Dec. 1996), 46(6), 343-63.*
Medline Abstract No. 1998029329, Rickels et al., Journal of Clinical Psychiatry, (1997) 58 Suppl. 11, 4-10.*
Cancer, Principles & Practice of Oncology, 6th Edition, published 2001 by Lippincott Williams & Wilkins, (PA), p. 515.*
Powell et al., "Antitumor alkaloids from *Cephalotaxus harringtonia*: Structure and Activity", Journal of Pharmaceutical Sciences, (1972), 61(8), pp. 1227-1230.*
Ausprunk, D.H., et al., "Migration and Proliferation of Endothelial Cells in Preformed and Newly Formed Blood Vessels During Tumor Angiogenesis," *Microvasc. Res.* 14(1):53-65 (Jul. 1977).
Fidler, J., et al., "The implications of angiogenesis for the biology and therapy of cancer metastasis," *Cell* 79(2):185-188 (Oct. 1994).
Folkman, J., "How is blood vessel growth regulated in normal and neoplastic tissue? G.H.A.," *Cancer Res.* 46(2):467-473 (Feb. 1986).
Folkman, J., "Tumor Angiogenesis," *Adv. Cancer Res.* 19:331-358 (1974).
Folkman, J., "What is the evidence that tumors are angiogenesis dependent?," *J. Natl. Cancer Inst.* 82(1):4-6 (Jan. 1990).
Gasparini, G., et al., "Clinical importance of the determination of tumor angiogenesis in breast carcinoma: much more than a new prognostic tool," *J. Clin. Oncol.* 13(3):765-782 (Mar. 1995).
O'Reilly, M., et al., "Angiostatin: a novel angiogenesis inhibitor that mediates the suppression of metastases by a Lewis lung carcinoma," *Cell* 79(2):315-328 (Oct. 1994).
Powell, R.G., "Antitumor alkaloids for *Cephalotaxus harringtonia*:structure and activity," *J. Pharm. Sci.* 61(8):1227-1230 (Aug. 1972).
Storgard, C.M., et al., "Decreased Angiogenesis and Arthritic Disease in Rabbits Treated with an αvβ3 Antagonist," *J. Clin. Invest.* 103(1):47-54 (Jan. 1999).
Walsh, D.A., et al., "Angiogenesis in the Pathogenesis of Inflammatory Joint and Lung Diseases," *Arthritis Res.* 3(3):147-153 (Feb. 2001).
Weidner, N., et al., "Tumor angiogenesis and metastasis—correlation in invasive breast carcinoma," *New Eng. J. Med.* 324(1):1-8 (Jan. 1991).
Wilkinson-Berka, J.L., et al., "The Interaction Between the Renin-Angiotensin System and Vascular Endothelial Growth Factor in the Pathogenesis of Retinal Neovascularization in Diabetes," *J. Vasc. Res.* 38(6):527-535 (Nov.-Dec. 2001).

(Continued)

*Primary Examiner*—Raymond J Henley, III
(74) *Attorney, Agent, or Firm*—Morgan Lewis & Bockius LLP; Richard F. Trecartin; Tuan N. Nguyen

(57) ABSTRACT

The invention relates to compositions and methods useful in treating or preventing angiogenic disease. The invention provides for compositions comprising cephalotaxine alkaloids as antiangiogenic agents for treatment of a host with an angiogenic disease or for prophylactic treatment of a host to inhibit the onset or progression of an angiogenic disease.

22 Claims, 5 Drawing Sheets

OTHER PUBLICATIONS

Luo, J. et al., 1998, "Differential Inhibition of Fluid Accumulation and Tumor Growth in Two Mouse Ascites Tumors by an Antivascular Endothelial Growth Factor/Permeability Factor Neutralizing Antibody[1]", *Cancer Research*, vol. 58, pp. 2594-2600.

Nagy, J. et al. 1995, "Pathogenesis of Ascites Tumor Growth: Angiogenesis, Vascular Remodeling, and Stroma Formation in the Peritoneal Lining[1]", *Cancer Research*, vol. 55, pp. 376-385.

Baguley, Bruce C., et al., "Comparison of the effects of flavone acetic acid, fostriecin, homoharringtonine and tumour necrosis factor α on colon 38 tumours in mice, " Eur. J. Cancer Clin Oncol., v. 25, n. 2, p. 263-269, 1989.

Fountzilas, G., et al., "The inhibitory effects of teniposide and homoharringtonine on the growth of pancreatic carcinoma cells in vitro," Anticancer Research, v. 8, n. 3, May-Jun. 1988.

Takano I. et al. Ester-type cephalotaxus alkaloids from cehpalotaxus harringtonia var. drupacea, Phytochemistry, Pergamon Press, GB, vol. 44, No. 4, Feb. 1997, pp. 735-738.

Tebbi, Cameron K., et al., "Modulation of drug resistance in homoharringtonine-resistant C-1300 neuroblastoma cells with cyclosporine A and dipyridamole," J. of Cellular Physiology, v. 148 p. 464-471, 1991.

Wilkoff, Lee J., et al., "Etoposide-resistant human colon and lung adenocarcinoma cell lines exhibit sensitivity to homoharringtonine," Cancer Chemother Pharmocol, v. 33, p. 149-153, 1993.

Zhang et al. "Inhibitory effects of homoharringtonine and hydroxycamptothecin in combination with other agents on cancer cell growth," Asia pacific Journal of Pharmacology, Singapore University Press, SG., vol. 7, 1992, pp. 191-195.

\* cited by examiner

The general chemical structure of the cephalotaxine family

The chemical structure of homoharringtonine

Schematic representation of CAM vessels

Effects of homoharringtonine in the CAM

Comparison between the qualitative changes caused by homoharringtonine and taxol. ( x 40; Day 5).

ANGIOGENESIS INHIBITION BY CEPHALOTAXINE ALKALOIDS, DERIVATIVES, COMPOSITIONS AND USES THEREOF

This application claims the benefit of U.S. Ser. No. 60/397,657, filed Jul. 22, 2002.

TECHNICAL FIELD

The invention relates to compositions and methods useful in treating or preventing angiogenic disease. The invention provides for compositions comprising cephalotaxine alkaloids as antiangiogenic agents for treatment of a host with an angiogenic disease or for prophylactic treatment of a host to inhibit the onset or progression of an angiogenic disease.

BACKGROUND OF THE INVENTION

Angiogenesis is defined as the formation and differentiation of new blood vessels. It has been linked to a number of diseases and conditions, in particular to cancer, inflammation and certain retinal disorders. Angiogenic diseases include, but are not limited to, solid tumors, diabetic retinopathy, inflammatory diseases (such as rheumatoid arthritis, osteoarthritis, asthma, and pulmonary fibrosis), macular degeneration, angiofibroma, neovascular glaucoma, arteriovenous malformations, nonunion fractures, lupus and other connective tissue disorders, Osler-Weber syndrome, atherosclerotic plaques, psoriasis, comeal graft neovascularization, Pyogenic granuloma, retrolental fibroplasia, scleroderma, granulations, hemangioma, trachoma, hemophilic joints, and vascular adhesions.

Angiogenesis inhibitors have recently become high profile agents in the fight against cancer, with several compounds, most notably angiostatin, endostatin, combretastatin, SU5416, TNP470, anti-VEGF compounds and others, have advanced into clinical trials as anticancer agents.

Angiogenesis, the process by which new blood vessels are formed, is essential for normal body activities including reproduction, development, and wound repair. Although the process is not completely understood, it is believed to involve a complex interplay of molecules that regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks, or, in some cases, decades. When necessary (such as during wound repair), these same cells can undergo rapid proliferation and turnover within a 5 day period (Folkman, J. and Shing, Y.; *J. Biol. Chem.*, 267(16), 10931-10934, and Folkman, J. and Klagsbrun, M. Science, 235, 442-447 (1987).

Although angiogenesis is a highly regulated process under normal conditions, many diseases (characterized as angiogenic diseases) are driven by persistent unregulated angiogenesis. Otherwise stated, unregulated angiogenesis may either cause a particular disease directly or exacerbate an existing pathological condition. For example, ocular neovacularization has been implicated as the most common cause of blindness and dominates approximately 20 eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of solid tumors are also dependent on angiogenesis (Folkman, J., (1986) *Cancer Research*, 46, 467-473, Folkman, J., (1989) *J. National Cancer Institute*, 82, 4-6, both of which are hereby expressly incorporated by reference). It has been shown, for example, that tumors that enlarge greater than 2 mm must obtain their own blood supply and do so by inducing the growth of new capillary blood vessels. Once these blood vessels become embedded in the tumor, they provide a means for the tumor to metastasize to different sites such as liver, lung or bone (Weidner, N. et al., (1991) *The New England Journal of Medicine*, 324(1), 1-8).

To date, several naturally occurring angiogenic factors have been described and characterized (Fidler, J., I. and Ellis, L. M., (1994) *Cell*, 79, 185-189). Recently, O'Reilly, et al. have isolated and purified a 38 kilodalton (kDa) protein from serum and urine of tumor-bearing mice that inhibits endothelial cell proliferation (O'Reilly, M et al., (1994) *Cell*, 79, 315-328 and International Application WO 95/29242, published Nov. 2, 1995). Microsequence analysis of this endothelial inhibitor showed 98% sequence homology to an internal fragment of murine plasminogen. Angiostatin, as the murine inhibitory fragment was named, was a peptide that included the first four kringle regions of murine plasminogen. A peptide fragment from the same region of human plasminogen (i.e. containing kringles 1-4) also strongly inhibited proliferation of capillary endothelial cells in vitro and in vivo. The intact plasminogen from which this peptide fragment was derived did not possess as potent an inhibitory effect.

Several angiogenesis inhibitors are currently under development for use in treating angiogenic diseases (Gasparini, G. and Harris, A. L., (1995) *J. Clin. Oncol.*, 13(3): 765-782), but there are disadvantages associated with these compounds. Suramin, for example, is a potent angiogenesis inhibitor but causes severe systemic toxicity at the doses required for antitumor activity. Compounds such as retinoids, interferons and antiestrogens are safe for human use but have weak antiangiogenic effects.

Thus, there is a need for compounds useful in treating angiogenic diseases in mammals. Additionally, there is a need for compounds useful in the prophylactic treatment of a host to prevent or inhibit the onset, progression or reoccurrence of angiogenic disease.

While several antiangiogenic inhibitors have been identified, improvements in clinical use are still sought. The invention described herein demonstrates the novel use of the cephalotaxine alkaloids and derivatives including homoharringtonine that can inhibit angiogenesis and thereby affect angiogenic diseases.

SUMMARY OF THE INVENTION

In accordance with the objects outlined above, the present invention provides compositions and methods that are effective in inhibiting unwanted angiogenesis. One aspect of the invention provides for a method of treatment of a host with an angiogenic disease, comprising contacting the host with a cephalotaxine in amount sufficient to inhibit angiogenesis. In one embodiment of the invention, the angiogenic disease is a disease other than a solid tumor. In further embodiments of the invention, the angiogenic disease is selected from the group consisting of an inflammatory disease, including rheumatoid arthritis, osteoarthritis, asthma, and pulmonary fibrosis; diabetic retinopathy; or macular degeneration.

In a preferred embodiment of the invention, the cephalotaxine used in the above methods comprises homoharringtonine (cephalotaxine, 4-methyl-2-hydroxy-2-(4-hydroxy-4-methyl pentyl) butanediocate ester. In a further preferred embodiment, the cephalotaxine comprises a homoharringtonine analog.

In a preferred embodiment of the invention, the cephalotaxine is administered to the host orally. In further preferred embodiments of the invention the celphalotaxine is administered to the host intravenously, topically, intravescularly, intraperitoneally, intramuscularly, intradermally, subcutaneously or intraarterially.

In another aspect, the invention provides for a method of prophylactic treatment of a host, comprising contacting the host with a cephalotaxine in amount sufficient to inhibit the onset or progression of an angiogenic disease. In one embodiment of this method, the angiogenic disease is cancer. In a further preferred embodiment, the angiogenic disease is cancer characterized by microtumors or micrometastatic cancer cells. In a further preferred embodiment, the angiogenic disease is an angiogenic disease other than cancer, such as an inflammatory disease, including rheumatoid arthritis, osteoarthritis, asthma, and pulmonary fibrosis; diabetic retinopathy; or macular degeneration.

In a preferred embodiment of the invention, the cephalotaxine used in the above methods comprises homoharringtonine (cephalotaxine, 4-methyl-2-hydroxy-2-(4-hydroxy-4-methyl pentyl) butanediocate ester. In a further preferred embodiment, the cephalotaxine comprises a homoharringtonine analog.

DETAILED DESCRIPTION

Methods and compositions are provided for (1) treatment of a host with an angiogenic disease, and (2) prophylactic treatment of a host to prevent the onset or progression of an angiogenic disease. In a preferred embodiment, the cephalotaxine provides an antiangiogenic effect.

A compound or chemical agent is an angiogenic inhibitor when it inhibits the formation of blood vessels.

Cephalotaxines are alkaloids extracted from skins, stems, leaves and seeds of *Cephalotaxus fortunei* Hook and other related species, such as *Cepholotaxus sinensis* Li, *C. hainanensis* and *C. wilsoniana*, including *C. oliveri* mast and *C. harringtonia* (Powell, R. G., (1972) *J. Pharm Sci.*, 61(8): 1227-1230).

As used herein, the term cephalotaxine includes all members of that chemical family including alkaloid derivatives of the Chinese evergreen, *Cephalotaxus fortunei* and analogs thereof. The cephalotaxine family is defined by chemical structure as set forth in FIG. 1.

Figure 1:
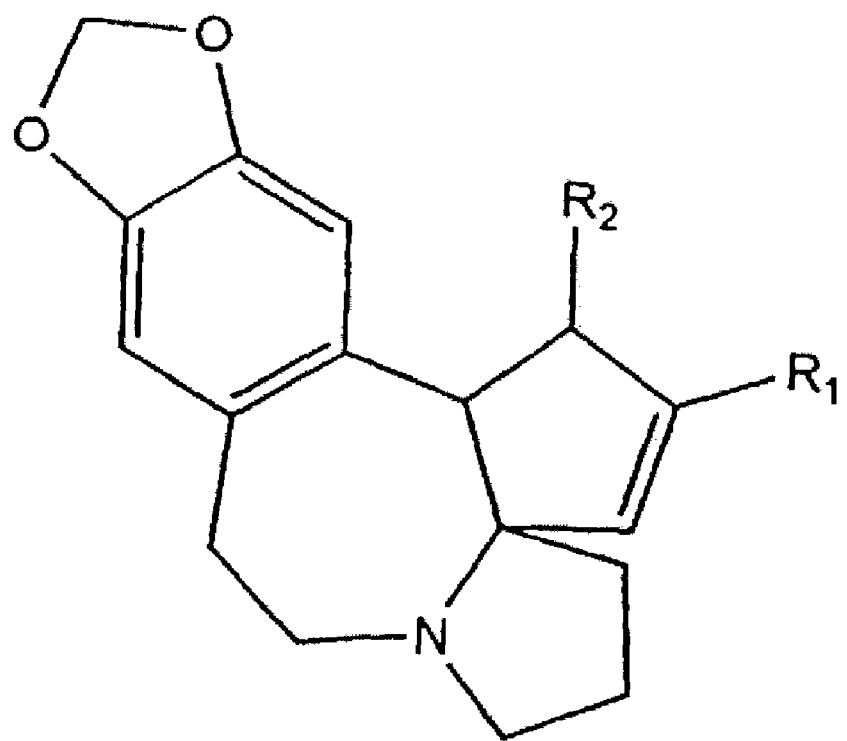
FIG. 1 depicts the general chemical structure of the cephalotaxine family.

A cephalotaxine analog is further defined but not limited to the structure depicted in FIG. 1, having substituent or substitute groups at R1 and R2. Examples of R1 and/or R2 include esters, including herringtonine, isoharringtonine, homoharringtonine, deoxyharringtonine, acetylcephalotaxine and the like. Table 1 lists structures of R1 and R2 for some of these analogs. R1 and R2 substitutions are typically employed to improve biological activity, pharmaceutical attributes such as bioavailability or stability, or decrease toxicity. In one embodiment, R1 and/or R2 include alkyl substitutions (e.g., methyl, ethyl, propyl etc.). In another embodiment, R1 and/or R2 include esters (e.g., methoxy, ethoxy, butoxy, etc.). R1 and R2 are not limited to the above examples, however, in the scope of this invention.

TABLE 1

| | R1 | R2 |
|---|---|---|
| isoharringtonine | —OCH₃ | |
| harringtonine | —OCH₃ | |
| acetylcephalotaxine | —OCH₃ | |
| homoharringtonine | —OCH₃ | |

Figure 2:
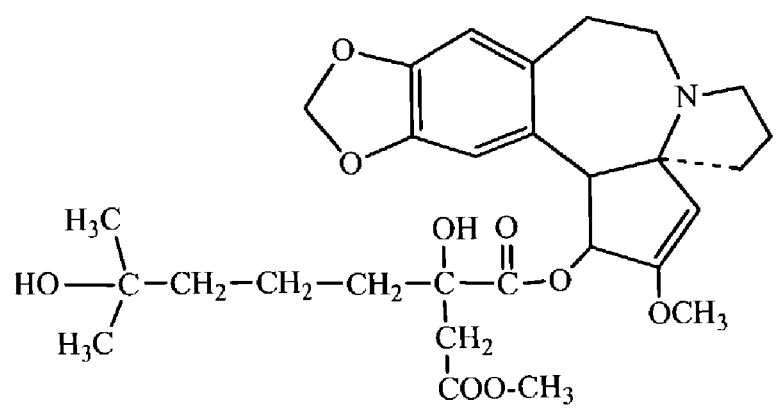
FIG. 2 depicts the chemical structure of homoharringtonine.

A cephalotaxine analog is a further chemical refinement. A specific example of cephalotaxine is homoharringtonine which is the butanediocate ester of cephalotaxine, 4-methyl-2-hydroxy-2-(4-hydroxy-4-methyl pentyl) (FIG. 2).

As is illustrated in the Examples, cephalotaxines are angiogenic inhibitors. It is an aspect of the invention to provide compositions comprising a cephalotaxine for use in treatment of a host with an angiogenic disease. It is a further aspect of the invention to provide compositions comprising a cephalotaxine for use in prophylactic treatments to prevent the onset or progression of an angiogenic disease.

Angiogenic diseases include, but are not limited to, solid tumors, diabetic retinopathy, inflammatory diseases (such as rheumatoid arthritis, osteoarthritis, asthma, and pulmonary fibrosis), macular degeneration, angiofibroma, neovascular glaucoma, arteriovenous malformations, nonunion fractures, lupus and other connective tissue disorders, Osler-Weber syndrome, atherosclerotic plaques, psoriasis, corneal graft neovascularization, Pyogenic granuloma, retrolental fibroplasia, scleroderma, granulations, hemangioma, trachoma, hemophilic joints, and vascular adhesions.

In one embodiment of the invention, a cephalotaxine is administered to a host with an angiogenic disease. The cephalotaxine is administered in an amount sufficient to inhibit angiogenesis thereby inhibiting progression of angiogenesis and the angiogenic disease.

In one embodiment of the invention, the angiogenic disease is a disease other than a solid tumor. In another embodiment of the invention the angiogenic disease is a solid tumor.

Growth and metastasis of tumors is dependent on angiogenesis. Solid tumors need oxygen and nutrients to survive and grow. Without a blood supply, potential tumors either die or remain dormant. These potential tumors can be, for example, microtumors or micrometastatic cancer cells. The "microtumors" remain as a stable cell population wherein dying cells are replaced by new cells. Microtumors may represent, for example, the initiation of a solid tumor in host that has no other solid tumors. Microtumors may also represent the remaining tumor cells present in a host after the solid tumor, from which the microtumors has metastasized, has been removed or eradicated. This condition may occur in a host that is in remission for cancerous tumors. Micrometastatic cancer cells refers to cancer cells that have not yet been vascularized to form a solid tumor.

The microtumor becomes a rapidly growing tumor when it becomes vascularized and can expand to 16,000 times its original volume in 2 weeks after vascularization. Without the blood supply, no growth is seen (Folkman, J. (1974) Tumor Angiogenesis, *Adv. Cancer Res.* 19: 331 358; Ausprunk, D. H. and Folkman, J. (1977) Migration and Proliferation of Endothelial Cells in Preformed and Newly Formed Blood Vessels During Tumor Angiogenesis, *Microvasc. Res.* 14: 53 65, both of which are hereby expressly incorporated by reference).

In addition to supplying the tumor with nutrients and oxygen, angiogenesis allows the solid tumor to metastasize. The new blood vessels provide a route that enables cells from the solid tumor to migrate to other sites in the host, resulting in the formation of secondary tumors.

Thus, by inhibiting angiogenesis, the vascularization of the microtumors is minimized and the progression of metastasis and tumor growth is inhibited or stopped.

In one embodiment of the invention, a cephalotaxine is administered to a host with microtumors. The cephalotaxine is administered in an amount sufficient to inhibit angiogenesis thereby inhibiting growth and metastasis of the microtumors. The microtumors may represent the early onset of a disease characterized by tumor growth. The microtumors may be the result of metastasis of an established solid tumor.

Another disease characterized by excessive blood vessel growth is diabetic retinopathy. Recent studies indicate a pathogenetic role for the renin-angiotensin system (RAS) and vascular endothelial growth factor (VEGF) in the eye in response to chronic hyperglycaemia (Wilkinson-Berka J. L., et al., (2001) The Interaction Between the Renin-Angiotensin System and Vascular Endothelial Growth Factor in the Pathogenesis of Retinal Neovascularization in Diabetes, *J Vasc Res.*, 38(6):527-35).

In one embodiment of the invention, a cephalotaxine is administered to a host with diabetes suffering from, or at the risk of suffering from, diabetic retinopathy. The cephalotaxine is administered in an amount sufficient to inhibit angiogenesis thereby slowing progression of the diabetic retinopathy.

Angiogenesis has been implicated in chronic inflammatory diseases, including for example, rheumatoid arthritis, osteoarthritis, asthma, and pulmonary fibrosis (Walsh, D. A. and Pearson' C. I. (2001), Angiogenesis in the Pathogenesis of Inflammatory Joint and Lung Diseases, *Arthritis Res.*, (3): 147-153; Storgard1, C. M., et al., (1999), Decreased Angiogenesis and Arthritic Disease in Rabbits Treated with an vβ3 Antagonist, *J Clin Invest*, 3(1):47-54, each of which is expressly incorporated by reference).

In one embodiment of the invention, a cephalotaxine is administered to a host with an inflammatory disease. The cephalotaxine is administered in an amount sufficient to inhibit angiogenesis thereby slowing progression of the inflammatory disease. In a preferred embodiment of the invention, the inflammatory disease is rheumatoid arthritis. In a further preferred embodiment, the inflammatory disease is osteoarthritis. In yet a further preferred embodiment, the inflammatory disease is asthma. In yet a further preferred embodiment, the inflammatory disease is pulmonary fibrosis.

In a further embodiment of the invention, a cephalotaxine is administered to a host as a prophylactic treatment. By "prophylactic treatment" is meant administration of a cephalotaxine to a host to prevent the onset or progression of an angiogenic disease. In one embodiment of the invention, a cephalotaxine is administered to a host to prevent the onset of tumor growth or metastasis or a disease characterized by tumor growth or metastasis. Such treatment may be desirable, for example, in a host that has exhibited tumor growth, such as a cancerous tumor, but is now in remission.

In a further preferred embodiment, a cephalotaxine is administered to a host to prevent the onset or progression of an angiogenic disease other than cancerous tumor growth. In one embodiment, the cephalotaxine is administered to a host at risk of exhibiting an inflammatory disease, such as rheumatoid arthritis, osteoarthritis, asthma, or pulmonary fibrosis.

In a further preferred embodiment, a cephalotaxine is administered to a host that is diabetic, or at risk of becoming diabetic, as a prophylactic treatment to prevent or inhibit the onset of diabetic retinopathy. In yet a further preferred embodiment, cephalotaxine is administered to a host that is at risk of exhibiting macular degeneration (such as an elderly human) as a prophylactic treatment to prevent or inhibit the onset of macular degeneration.

For the prophylactic treatments above, the cephalotaxine is administered in amount sufficient to inhibit the onset or progression of the angiogenic disease.

The compounds of the invention described above can be provided as pharmaceutically acceptable formulations using formulation methods known to those of ordinary skill in the art. These formulations can be administered by standard routes. In general, the compounds may be administered orally, intravenously, topically, intravescularly, intraperitoneally, intramuscularly, intradermally, subcutaneously or intraarterially. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441-446 (1991).

The dosage of the compound will depend on the condition being treated, the particular compound, and other clinical factors such as weight and condition of the human or animal and the route of administration of the compound. It is to be understood that the present invention has application for both human and veterinary use.

In one embodiment of the invention, the cephalotaxine is administered to a host in the range of 0.05-5.0 mg/m$^2$. In a preferred embodiment, the cephalotaxine is administered to a host in the range of 0.1 to 3.0 mg/m$^2$. In a further preferred embodiment, the cephalotaxine is administered to a host in the range of 0.1-1.0 mg/m$^2$.

The cephalotaxine may be administered biweekly, weekly, daily, twice daily, or more frequently as required to inhibit angiogenesis or to inhibit the onset or progression of an angiogenic disease.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein for minutes to hours to days.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents Additionally, the cephalotaxine composition of the invention may be administered with other active compounds. Examples of active compounds that may be co-administered with the cephalotaxine composition include, but are not limited to, other antiangiogenic agents such as angiostatins, VEGF inhibitors, endostatins, combretastatins, 2-methoxyestradiol, thalidomide and Avastatin™, taxanes, antimetabolites such as methotrexate, corticosteroids, colchicine and analogs, antibodies against angiogenic targets, interferon, diabetic regulating agents such as insulin and insulin growth factor inhibitors, anti-inflammatory agents such as COX-2 inhibitors, anti-arthritics, aspirin, ibuprofen, naprosyn and the like, gene therapy, antisense therapy, and RNA interference therapy against gene targets and associated mRNA and protein targets of angiogenesis, antisense therapy, and RNA interference therapy.

The active ingredient may administered to the host before, during or after administration of the cephalotaxine composition. In one embodiment of the invention, the active ingredient is mixed with the cephalotaxine prior to administration and the mixture is administered to the host. In a further embodiment, the active ingredient and the cephalotaxine are administered separately but simultaneously to the host. In yet a further embodiment, the active ingredient is administered before the cephalotaxine. In a preferred embodiment, the active ingredient is administered before the cephalotaxine with the active ingredient still present systemically in the host. In yet a further embodiment, the active ingredient is administered after the cephalotaxine. In a preferred embodiment, the active ingredient is administered after the cephalotaxine while the cephalotaxine is still present systemically in the host.

Suitable hosts of the invention include humans or other animals.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are hereby expressly incorporated by reference.

EXAMPLES

Example 1

Effects of Homoharringtonine in the CAM Assay

Protocol:

Fertilized chicken eggs (HiChick Breeding Co, Kapunda, South Australia) were incubated for three days at 38° C. On Day 3 the embryos were cracked out of the egg and into a cup made of plastic piping, with plastic film stretched over the top to form a hammock for the egg to be suspended in. Two ml of DMEM containing penicillin and streptomycin was added to each cup prior to the egg being added. A Petri dish on the top maintained sterility. Incubation continued in a humidified 37° C. incubator.

On Day 4 the chorioallantoic membrane (CAM) begins to grow, and pictures were taken of each embryo at ×5 to measure the CAM area using image analysis software (Video Pro 32, Leading Edge Pty Ltd, South Australia). Embryos were then grouped according to their CAM area, with a control embryo in each for comparison. There were four matched embryos, treated with 6.25, 12.5 and 25 ng of homoharringtonine. Grouping is critical as in these early developmental stages changes in the CAM growth are dramatic. Relatively small differences in size on Day 4 translate to large differences in the CAM on Day 5, making it impossible to compare treatments. Substances were applied in methylcellulose discs, which were first dried under vacuum overnight. The methylcellulose discs were applied to the top of the CAM, and at the beginning of treatment were at least three to four-fold bigger than the CAM area, meaning treatment covered the entire CAM surface.

On Day 5 skim milk with contrast medium was injected into the CAM. Pictures were then taken at various levels of magnification up to ×63. Quantitative measurements were made from ×5 pictures. CAM area, and vein and artery lengths were measured using image analysis (Video Pro 32, Leading Edge Pty Ltd, South Australia). Relative vessel lengths were then calculated as the total length/CAM area. Statistical analysis was made using SigmaStat and OneWay ANOVA with $p<0.05$ as the level of significance.

Figure 3:
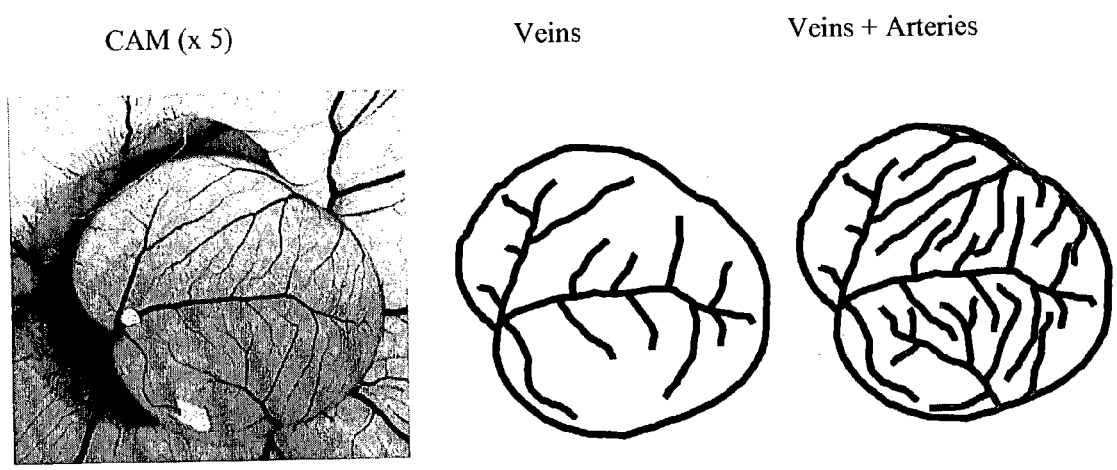
FIG. 3 depicts a schematic representation of chorioallantoic membrane (CAM) vessels.

The normal organization of the CAM is uniform, with the major vein draining towards the left, and the artery branches coming over the edge of the top and bottom of the CAM. FIG. 3 schematically illustrates tracing of the vein and artery branches, as performed for the measurement of vessel lengths.

The angiogenic inhibitor, homoharringtonine, was obtained from ChemGenex Therapeutics, Inc. (Menlo Park, Calif.) and was made to the appropriate concentration in sterile water. At the initial doses that were used homoharringtonine resulted in the death of the embryos, hence the dose was reduced. Homoharringtonine was applied at 6.25, 12.5 and 25 ng (11.3, 22.5 and 45 nM) doses, and compared with water treated controls. Results are shown in Table 2. Homoharringtonine reduced the growth of the CAM to 42% of the control in the 25 ng treated CAM. The vein, artery and total vessel lengths were also significantly reduced in the 25 ng group, with non significantly reduced vessel lengths in the 6.25 and 12.5 ng treated groups. The vein, artery and total vessel lengths were reduced to 15%, 18% and 17% of control, respectively. Not surprisingly the relative vessel lengths were also reduced, with the relative artery lengths being significantly reduced at all three dose levels of homoharringtonine, and the relative vein and total vessel lengths significantly different only at the highest dose of homoharringtonine.

TABLE 2

Homoharringtonine (6.25, 12.5 and 25 ng versus DMSO control; Mean +/− SEM)

|  | Water n = 6 | 6.25 ng n = 6 | 12.5 ng n = 6 | 25 ng n = 6 |
|---|---|---|---|---|
| CAM area (pixels) | | | | |
| Day 4 | 6.1 ± 1.4 | 6.5 ± 1.6 | 6.3 ± 1.6 | 6.2 ± 1.5 |
| Day 5 | 65.3 ± 18.3 | 45.3 ± 11.6 | 53.0 ± 11.6 | 30.2 ± 9.9 |
| CAM increase (fold) | 10.2 ± 0.8 | 7.0 ± 0.4$^a$ | 9.0 ± 1.0$^b$ | 4.3 ± 0.7$^a$ |
| Vessel lengths (pixels) | | | | |
| Vein length | 2382 ± 717 | 1482 ± 499 | 1564 ± 427 | 359 ± 143$^a$ |
| Artery length | 3009 ± 884 | 1573 ± 516 | 1787 ± 544 | 551 ± 265$^a$ |
| Total vessel length | 5391 ± 1596 | 3055 ± 1003 | 3351 ± 953 | 909 ± 396$^a$ |
| Relative vessel lengths (length/CAM area) | | | | |
| Relative vein length | 36.2 ± 4.9 | 31.6 ± 4.6$^b$ | 28.3 ± 4.4$^b$ | 11.3 ± 3.5$^a$ |
| Relative artery length | 45.1 ± 1.6 | 31.6 ± 4.5$^{ab}$ | 31.8 ± 3.7$^{ab}$ | 13.0 ± 4.3$^a$ |
| Relative total vessel length | 81.4 ± 6.1 | 63.2 ± 7.7$^b$ | 60.1 ± 7.5$^b$ | 24.3 ± 6.7$^a$ |

$^a$p < 0.05 vs control;
$^b$p < 0.05 vs 25 ng

Figure 4:
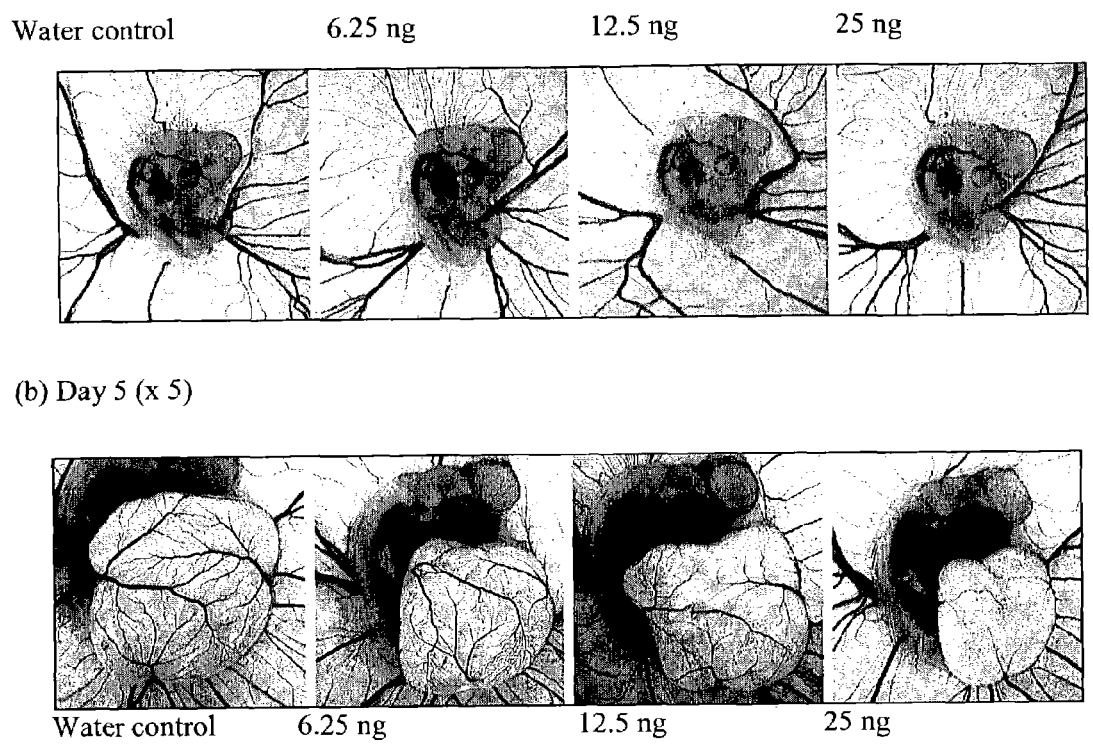
FIG. 4 depicts effects of homoharringtonine in the CAM.

Homoharringtonine treatment of the CAMs resulted in a significant reduction in blood vessels, as illustrated in FIG. 4.

As seen in FIG. 4, even at the lowest dose of homoharringtonine the CAM is smaller and the normal vessel organization disturbed. Note the overlaying of a major vein and artery branch at the bottom of the CAM. The CAM at 12.5 ng has a general reduction in vessels without a great deal of disturbance in the organization. The highest dose of 25 ng resulted in only fine vestigial blood vessels remaining, and blood vessel development almost completely blocked. The 25 ng dose killed one of the smaller embryos.

Figure 5:
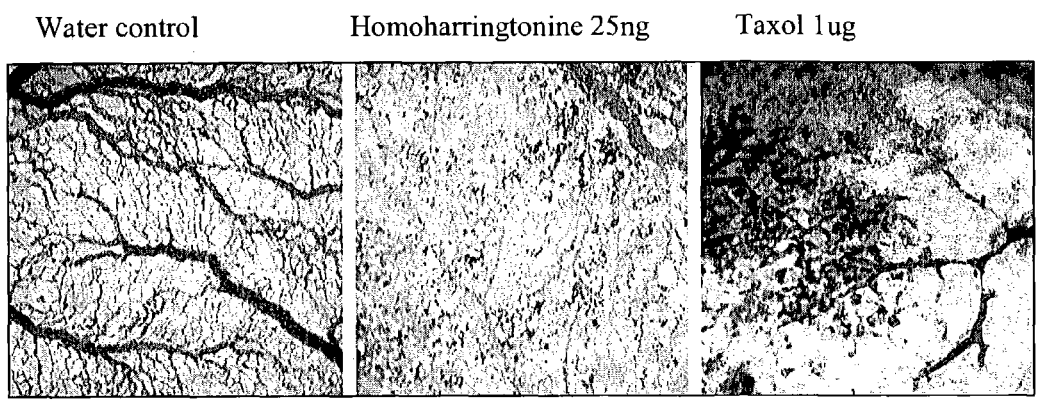
FIG. 5 depicts the comparison between qualitative changes caused by homoharringtonine and taxol.

The changes seen due to homoharringtonine at higher magnifications were unique, and unlike other substances that have been tested. In FIG. 5 a normal CAM and 25 ng homoharringtonine treated CAM are shown. The water control is well vascularized. Homoharringtonine treatment has resulted in a dramatic reduction in blood flow, with only a few fine vessels in the field carrying red blood cells. The unique feature is the black dots spread through the field of view representing red blood cells that have been trapped in blood vessels in which flow has ceased. Compare this to the changes seen with taxol, with diffuse leakage of the red blood cells outside the vessels and the skeletons of larger vessels with no remaining blood flow.

The antiangiogenic activity of homoharringtonine was tested using the early chicken chorioallantoic membrane (CAM). The use of homoharringtonine resulted in significant reductions in blood vessel development in the CAM, with differences in both the potency and the qualitative changes observed from that of taxol. These differences may reflect varying mechanisms of action, such as affecting endothelial cell proliferation, apoptosis, and migration due to these substances.

What is claimed is:

1. A method of treating a host with an angiogenic disease, consisting essentially of contacting said host with a cephalotaxine in an amount sufficient to inhibit angiogenesis associated with said angiogenic disease, wherein said angiogenic disease is not a solid tumor and wherein said angiogenesis associated with said angiogenic disease is inhibited in said host.

2. The method of claim 1 wherein the angiogenic disease is selected from the group consisting of an inflammatory disease, diabetic retinopathy, or macular degeneration, angiofibroma, neovascular glaucoma, arteriovenous malformation, nonunion fracture, connective tissue disorder, Osler-Weber syndrome, atherosclerotic plague, psoriasis, corneal graft neovascularization, Pyogenic granuloma, retrolental fibroplasia, scleroderma, granulations, hemangioma, trachoma, hemophilic joints and vascular adhesions.

3. The method of claim 2 wherein the inflammatory disease is selected from the group consisting of rheumatoid arthritis, osteoarthritis, asthma, and pulmonary fibrosis.

4. The method of claim 1 wherein the cephalotaxine comprises homoharringtonine (cephalotaxine, 4-methyl-2-hydroxy-2-(4-hydroxy-4-methylpentyl) butanedioate ester).

5. The method of claim 1 wherein the cephalotaxine comprises a compound of the formula

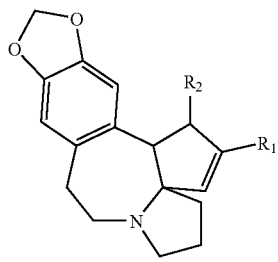

wherein $R_1$ is an ester or an alkyl and wherein $R_2$ is an ester or an alkyl.

6. The method of claim 1, wherein said contacting is by a route selected from the group consisting of oral, intravenous, topical, intravesicular, intraperitoneal, intramuscular, intradermal, subcutaneous and intraarterial.

7. A method of inhibiting the onset or progression of an angiogenic disease in a host, consisting essentially of contacting said host with a cephalotaxine in an amount sufficient to inhibit the onset or progression of an angiogenic disease, wherein angiogenesis associated with said angiogenic disease is inhibited in said host.

8. The method of claim 7, wherein the angiogenic disease is cancer.

9. The method of claim 8, wherein the cancer is characterized by cancer cells that have not yet been vascularized to form a solid tumor.

10. The method of claim 7, wherein the angiogenic disease is an angiogenic disease other than cancer.

11. The method of claim 7, wherein the angiogenic disease is selected from the group consisting of an inflammatory disease, diabetic retinopathy, or macular degeneration, angiofibroma, neovascular glaucoma, arteriovenous malformation, nonunion fracture, connective tissue disorder, Osler-Weber syndrome, atherosclerotic plague, psoriasis, corneal graft neovascularization, Pyogenic granuloma, retrolental fibroplasia, scieroderma, granulations, hemangioma, trachoma, hemophilic joints and vascular adhesions.

12. The method of claim 11, wherein the inflammatory disease is selected from the group consisting of rheumatoid arthritis, osteoarthritis, asthma, and pulmonary fibrosis.

13. The method of claim 7, wherein the cephalotaxine comprises homoharringtonine (cephalotaxine, 4-methyl-2-hydroxy-2-(4-hydroxy-4-methylpentyl) butanedioate ester).

14. The method of claim 7, wherein the cephalotaxine comprises a compound of the formula

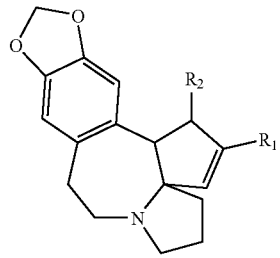

wherein $R_1$ is an ester or an alkyl and wherein $R_2$ is an ester or an alkyl.

15. The method of claim 5 or 14, wherein said cephalotaxine is selected from the group consisting of harringtonine, isohaningtonine, homoharringtonine, deoxyharringtonine, and acetylcephalotaxine.

16. A method of treating a host with an angiogenic disease comprising contacting said host with a cephalotaxine in an amount sufficient to inhibit angiogenesis associated with said angiogenic disease,
  wherein said angiogenic disease is selected from the group consisting of diabetic retinopathy, inflammatory disease, macular degeneration, angiofibroma, neovascular glaucoma, arteriovenous malformation, nonunion fracture, lupus, Osler-Weber syndrome, atherosclerotic plaque, psoriasis, corneal graft neovascularization, Pyogenic granuloma, retrolental fibroplasia, scieroderma, granulations, trachoma, hemophilic joints and vascular adhesions; and
  wherein said angiogenesis associated with said angiogenic disease is inhibited in said host.

17. The method of claim 16 wherein said inflammatory disease is selected from the group consisting of osteoarthritis, asthma, and pulmonary fibrosis.

18. The method of claim 2 or 11 or wherein said connective tissue disorder is lupus.

19. The method of claim 16 wherein said cephalotaxine comprises a compound of the formula

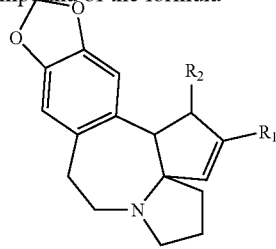

wherein $R_1$ is an ester or an alkyl and wherein $R_2$ is an ester or an alkyl.

20. The method of claim 16 wherein said cephalotaxine is selected from the group consisting of harringtonine, isoharringtonine, homoharringtonine, deoxyharringtonine, and acetylcephalotaxine.

21. The method of claim 20 wherein said cephalotaxine is homoharringtonine (cephalotaxine, 4-methyl-2-hydroxy-2-(4-hydroxy-4-methylpentyl) butanedioate ester).

22. The method of claim 16, wherein said contacting is by a route selected from the group consisting of oral, intravenous, topical, intravesicular, intraperitoneal, intramuscular, intradermal, subcutaneous and intraarterial.

* * * * *